US007875074B2

(12) United States Patent
Chen et al.

(10) Patent No.: US 7,875,074 B2
(45) Date of Patent: Jan. 25, 2011

(54) NATURALLY CONTOURED, PREFORMED, THREE DIMENSIONAL MESH DEVICE FOR BREAST IMPLANT SUPPORT

(75) Inventors: Gaoyuan Gavin Chen, Hillsborough, NJ (US); James Matrunich, Mountainside, NJ (US); Robert J. Tannhauser, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 39 days.

(21) Appl. No.: 12/233,991

(22) Filed: Sep. 19, 2008

(65) Prior Publication Data

US 2009/0082864 A1 Mar. 26, 2009

Related U.S. Application Data

(60) Provisional application No. 60/994,434, filed on Sep. 19, 2007.

(51) Int. Cl.
*A61F 2/12* (2006.01)
*A61F 2/00* (2006.01)
*A61B 17/08* (2006.01)

(52) U.S. Cl. .............................. 623/8; 600/37; 606/151

(58) Field of Classification Search ..................... 623/8; 600/37; 606/151
See application file for complete search history.

(56) References Cited

U.S. PATENT DOCUMENTS 3,799,174 A * 3/1974 Howard ....................... 450/40
4,936,858 A * 6/1990 O'Keeffe ....................... 623/8
6,210,439 B1 4/2001 Firmin
6,951,534 B2 10/2005 Girard et al.
2004/0143154 A1* 7/2004 Lau et al. ...................... 600/37
2005/0014992 A1* 1/2005 Lilip et al. .................... 600/37
2006/0030939 A1 2/2006 Frank
2006/0167338 A1* 7/2006 Shfaram ...................... 600/37
2007/0088434 A1* 4/2007 Frank ............................ 623/8
2007/0198085 A1* 8/2007 Benslimane ................... 623/8
2010/0191330 A1* 7/2010 Lauryssen et al. .............. 623/8

FOREIGN PATENT DOCUMENTS

WO WO 2004/096098 A1 11/2004
WO WO 2006/017834 A 2/2006
WO WO 2006/117622 A1 * 11/2006
WO WO 2007/004214 A 1/2007
WO WO 2007004214 A2 * 1/2007

* cited by examiner

*Primary Examiner*—David Isabella
*Assistant Examiner*—Andrew Iwamaye

(57) ABSTRACT

A preformed, seamless, three-dimensional, anatomically contoured prosthetic device for reinforcing breast tissue and supporting a breast implant includes a flat back wall, a concave front wall and a curved transitional region between the flat back wall and the front wall defining a smoothly curved bottom periphery. A concave receiving space is defined by the back wall and the front wall for at least partially receiving and supporting the breast implant therein. The three-dimensional prosthetic device is free of wrinkles, creases, folds or seams, which may have otherwise caused potential tissue irritation, bacteria hosting, infection and palpability problems.

4 Claims, 10 Drawing Sheets

14 9 7 11 10 12 2 13

NATURALLY CONTOURED, PREFORMED, THREE DIMENSIONAL MESH DEVICE FOR BREAST IMPLANT SUPPORT

CROSS-REFERENCE TO RELATED APPLICATION

This application claims the benefit of U.S. Provisional Application Ser. No. 60/994,434, filed on Sep. 19, 2007.

BACKGROUND OF THE INVENTION

1. Field of the Invention

The present invention relates generally to prosthetic devices for supporting or maintaining the position of mammalian tissue, and more particularly relates prosthetic support devices for breast tissue or breast implants.

2. Description of the Prior Art

Breast implants are conventionally and commonly used in a plurality of cosmetic and reconstructive surgeries. One of the most prevalent complications arising in the post-operative stage of the surgery is the displacement of the implant. Implants are prone primarily to three different malpositions: inferior, lateral and symmastia. When an implant is displaced inferiorly, also referred to as "bottoming out", the distance from the nipple to the inframammary fold is increased. Lateral displacement results in the implant falling into the axilla. In the case of symmastia, the implant moves medially on the chest wall. The displacement of breast implants may be attributed to several factors including: surgical error, the gravity of the implant or the general weakness of the supporting tissue. Surgical error often results from the over-dissection of muscle and tissue while creating the pocket for the implant, which is thus inappropriately oversized.

The commonly accepted method for correcting malpositioned implants is capsulorrhaphy. Capsulorrhaphy relies on the capsule or scar tissue to repair and support a repositioned implant. As with many surgical correction procedures, capsulorrhaphy has inherent disadvantages and problems. The procedure generally requires a significant amount of time which can place undue stress upon a patient. For example, very often it can take 1.5 to several hours to repair one malpositioned implant due to the tedious process of making numerous suture bites with the capsules to close part of an improperly sized pocket due to dissection or other causes. Implant displacement can also be recurrent because the natural tissue and/or thin capsules of the patient's body may be or become too weak to support the breast implant using capsulorrhaphy. Several conventional methods and apparatuses have been developed to support implants and breast tissue.

Surgical meshes are an example of a device used for supporting, repairing or reinforcing tissue, or supporting and/or maintaining the position of natural anatomical structures (e.g. the heart or breast tissue), or certain anatomical replacement structures (e.g. breast implants). More specifically, surgeons have used two-dimensional porous sheets or surgical meshes for supporting breast implants or supporting natural breast tissue. An example of such is disclosed in U.S. Patent Application Publication No. US2006/0030939 by applicant Robert E. Frank. The Frank published patent application discloses an implantable prosthesis for positioning and supporting a breast implant. The prosthesis is formed from a flat mesh which is cut to a desired geometry or dimensions, and the edges are then sewn or sutured together to form a sling-shaped receiving area for receiving the breast implant. As shown in FIGS. 7 and 8 and in paragraph [0034] and [0035] of the Frank published patent application, the first portion 14 and the second portion 16 are formed from a sheet 12 of a prosthetic material, with the first and second portions 14, 16 separated by a fold line 18. The side walls 24, 26 of the first portion 14 and the side walls 30, 32 of the second portion 16 are fixed together by sutures, a suitable adhesive or tacking to maintain the shape of the implantable prosthesis.

There are several disadvantages with the prosthesis disclosed in US2006/0030939. For one, shaping and folding a two-dimensional sheet or mesh to form a three-dimensional prosthesis is cumbersome, and it is also often difficult to obtain the desired three-dimensional shape. Also, cutting and trimming a mesh product to fit the size or contour of a breast implant in an operating room may add additional technical difficulties, prolong the surgeon's operation time and create fine, albeit sterile, dust, which is a byproduct that is undesirable to have in a clean operating room. Furthermore, sewing or suturing folded mesh edges together may result in the formation of stiff seams, which may generate palpability problems or may interfere with the detection of breast cancer tumors. Additionally, the existence of mesh folds, wrinkles or seams in the sewn together prosthesis or support may increase the chance of hosting bacteria and the risk of infection at the surgical site. In addition, the mesh prosthesis or support may collapse under its own weight after it is sewn into its desired form, causing the handling of the mesh to be more cumbersome than it would be if the mesh could maintain its shape naturally.

U.S. Pat. No. 6,951,534, which issued to Michael J. Girard et al., discloses an elastic cardiac support device which is constructed from a biocompatible mesh material. The device is stated to be highly compliant, and can fit to and comply with the shape of the heart when the heart is positioned within the device. However, if there is no anatomical structure within the support device, the device cannot hold its shape because of a lack of rigidity or stiffness.

OBJECTS AND SUMMARY OF THE INVENTION

It is an object of the present invention to provide a seamless, three-dimensional, anatomically contoured prosthetic device for reinforcing breast tissue and supporting a breast implant.

It is another object of the present invention to provide a three-dimensional mesh device that can reduce the duration of a given surgical procedure, as there is no need to alter or manipulate the size or shape of the device when it is properly selected for a given breast implant.

It is yet another object of the present invention to provide a preformed three-dimensional mesh device having a smoothly curved bottom periphery that provides a natural fit to the contour of a breast implant to be supported by the device without the need for cutting or trimming the device in the operating room.

It is still another object of the present invention to provide a three-dimensional mesh device that has a semi-doughnut shape for ease of accommodating breast implants of various sizes, shapes or projections with minimum or no alteration of the device being required.

It is a further object of the present invention to provide a three-dimensional mesh device that has no seams, folds or wrinkles which, therefore, minimizes palpability, bacterial hosting and the risk of infection.

It is yet a further object of the present invention to provide a three-dimensional mesh device for reinforcing breast tissue and supporting a breast implant which includes a flat back wall to allow for ease of handling, storage or deployment of the device during a surgical procedure.

It is still a further object of the present invention to provide a three-dimensional, anatomically contoured prosthetic mesh device which has a resiliency sufficient to support its own weight and maintain its shape.

It is yet a further object of the present invention to provide a three-dimensional mesh device that may include a temporary shape-holding element attached to it to further increase the rigidity of the three-dimensional mesh.

It is another object of the present invention to provide a three-dimensional mesh device having a temporary-shape holding element attached to it, which shape-holding element may be removed upon completion of the fixation of the mesh device.

It is still another object of the present invention to provide a three-dimensional mesh device which may include a coating agent or a pulling string that will promote the deployment of the device and keep the device from sticking together.

It is another object of the present invention to provide a three-dimensional mesh device which may include distinguishable colored markings that will help show the geometric center or edges of the device for ease of orientation and fixation of the device.

It is yet another object of the present invention to provide a preformed, seamless, three-dimensional, anatomically contoured prosthetic device for reinforcing breast tissue and supporting a breast implant which overcomes the inherent disadvantages of conventional breast implant supports.

In accordance with one form of the present invention, a seamless, three-dimensional, anatomically-contoured prosthetic device for reinforcing breast tissue and supporting a breast implant includes a flat back wall and a concave front wall joined seamlessly to the back wall at the bottom portions of both to define a semi-circular periphery at the joined bottom portions. The top edge of the back wall may be straight, and preferably the top edge of the front wall is curved or shaped, or temporarily folded partially during fixation, so that at least part of the back wall is exposed for ease of fixating the back wall to the tissue. Together, the back wall and front wall define an open pocket for receiving and supporting at least a portion of a breast implant or breast tissue therein.

In accordance with another form of the present invention, a preformed, seamless, three-dimensional, anatomically contoured prosthetic device has the shape of a half-doughnut formed, again, with a relatively flat back wall joined to a curved, preferably slightly lower front wall. The two walls are joined together at their bottom portions to define the bottom periphery of the device with a semi-circular or smoothly curved contour, with no seams or folds in the preformed device.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

The implantable prosthesis constructed in accordance with the present invention preferably is a preformed, seamless, three-dimensional, anatomically contoured device used for reinforcing breast tissue and supporting a breast implant. The prosthetic device is preferably formed from a mesh material 2.

Figure 1:
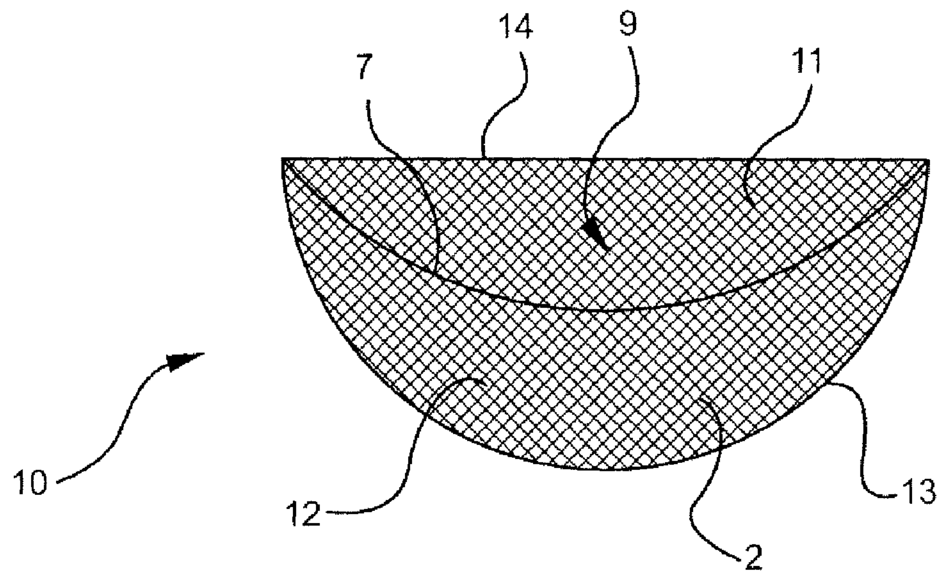
FIG. 1 is a front view of a semi-round, three-dimensional, seamless implantable prosthesis formed in accordance with the present invention.

FIG. 1 illustrates a first preferred form of the preformed, seamless, three-dimensional, anatomically contoured prosthetic device 10 of the present invention. The prosthetic device includes a flat back wall 11 having a top rim or edge 14 and a bottom portion situated opposite the top rim or edge 14. The prosthetic device further includes a front wall 12, the front wall being situated opposite the back wall 11 and also having a top rim or edge 7 and a bottom portion situated opposite the top edge 7. The two bottom portions of the front wall 12 and the back wall 11 are joined together to define a seamless, semi-circular periphery 13 at the bottom of the prosthetic device 10.

The top edge 7 of the front wall 12 and the upper portion of the front wall 12 are spaced apart from the top rim 14 of the back wall 11 and the upper portion of the back wall 11 so as to define a concave or semi-round receiving space or pocket 9 that is naturally formed and can readily conform to the contour of a breast implant at least partially receivable therein. This minimizes or negates the need to trim and manipulate the device to reshape it in the sterile environment of the operating room during a surgical procedure.

The back and front walls 11, 12 may be formed concurrently using a thermal forming process or the like so that no seams or folds are present in the formed prosthesis. The radius of the semi-circular periphery 13 at the bottom of the prosthesis is preferably in the range of about five (5) centimeters to about twelve (12) centimeters, and even more preferably in the range of about five (5) centimeters to about ten (10) centimeters. Based on the relative size of the breast implant to be supported, the surgeon can choose a three-dimensional prosthetic device 10 having a proper radius, which is about the same as or, more preferably, slightly greater than that of the breast implant.

As can be seen from FIG. 1 of the drawings, the top rim 14 of the back wall 11 is preferably straight laterally across the width of the back wall. The top edge 7 of the front wall 12, however, is preferably curved or shaped so that at least some portions of the back wall 11 are not blocked by the the front wall 12. Having the back wall 11 flat and higher than the front wall 12 of the prosthetic device 10 formed in accordance with the present invention offers several advantages over conventional designs. First, the flat back wall 11 of the prosthetic device 10 may be readily laid on any flat surface without pressing and deforming the concave front wall 12. Second, having differing shapes and heights between the front wall 12 and the back wall 11 makes it easier for a surgeon to deploy and orient the prosthetic device 10 during the surgical procedure. Third, the "exposed" top portion of the back wall 11 (i.e., the portions that are not blocked by the front wall 12), allows a surgeon easy access for taking suture bites and affixing the prosthetic device 10 to the chest wall or the muscle of the patient inside the breast implant pocket which is formed during the surgical procedure.

Figure 2:
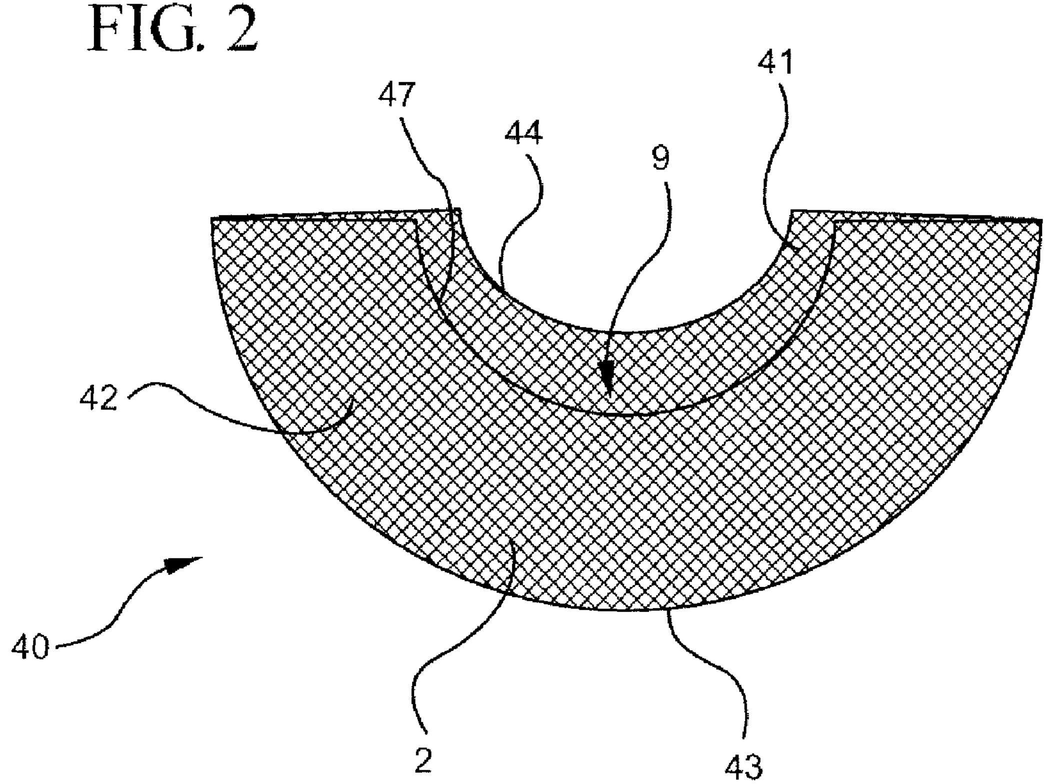
FIG. 2 is a front view of a semi-donut shaped, three-dimensional, seamless implantable prosthesis formed in accordance with a second embodiment of the present invention.
Figure 3A:
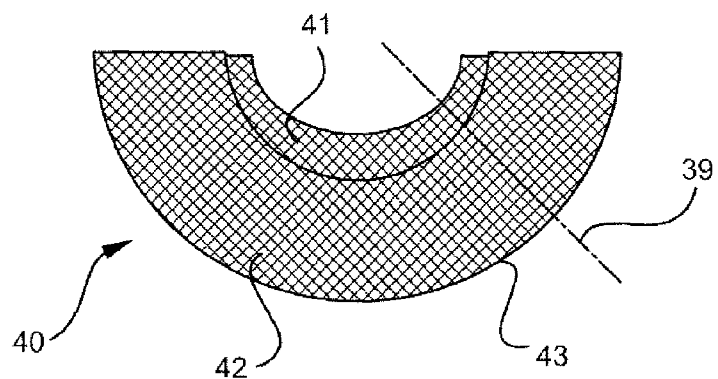
FIGS. 3*a*-3*d* are a sequence of front views of the semi-donut shaped, three-dimensional, seamless implantable prosthesis formed in accordance with the second embodiment of the present invention and illustrating a method of modifying the size of the prosthesis to fit a small breast implant.
Figure 3B:
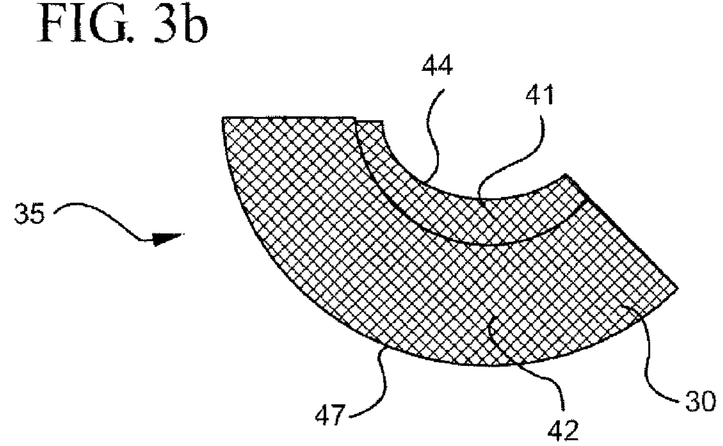
Figure 3C:
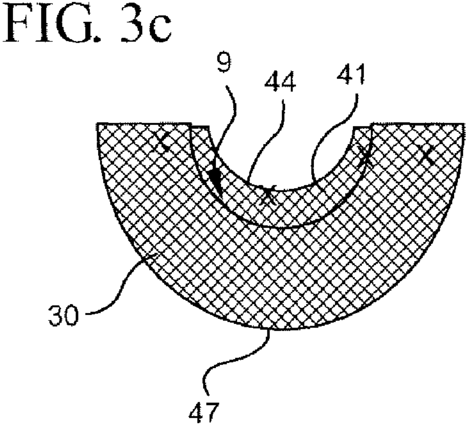
Figure 3D:
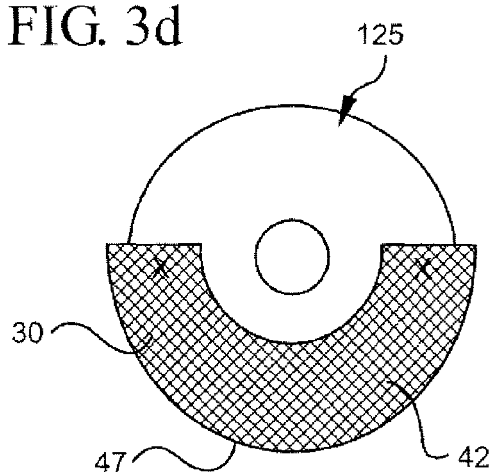

FIG. 2 illustrates a second preferred embodiment of the prosthetic device of the present invention. In this embodiment, prosthetic device 40 may have the general shape of a half-doughnut, that is, a semi-circular toroid, except that the back wall 41 is preferably relatively flat, as in the earlier embodiment shown in FIG. 1. The back wall 41 includes a top edge or rim 44 and a bottom portion. The semi-circular, toroidal-shaped prosthetic device 40 further includes a front wall 42, also having a top rim or edge 47 and an opposite bottom portion. Thus, the two bottom portions of the back wall 41 and the front wall 42 are seamlessly joined together to provide a semi-circular bottom periphery 43 for the prosthetic device 40. The front wall 42 is spaced apart from the back wall 41, especially at the top edge 47 at the front wall and the top rim 44 of the back wall and over the upper portions of each to define a pocket or receiving space 9 for at least partially receiving and supporting a breast implant. The concave or semi-round receiving space 9 defined by the back and front walls 41, 42 is thus naturally formed and can readily conform to the contour of the breast implant received therein. Again, such structure of the prosthetic device 40 of the present invention minimizes the need to trim or manipulate the prosthetic device 40 in order to reshape the device in the sterile environment of the operating room during a surgical procedure.

As can be seen from FIG. 2 of the drawings, the top edge 47 of the front wall 42 is preferably lower than the top rim 44 of the back wall 41. As also can be seen from FIG. 2, the bottom periphery 43 has a semi-circular or smoothly curved contour. As in the first embodiment, the prosthetic device 40 formed in accordance with the second embodiment of the present invention may be manufactured by a thermal forming process so that no seams or folds are present. Also, like the first embodiment, the prosthetic device 40 is preferably formed from a mesh material 2.

The radius of the semi-circular periphery 43 of the prosthesis 40 shown in FIG. 2 may be selected based on the size of the breast implant. However, in addition to having all of the advantages of the prosthetic device 10 formed in accordance with the first embodiment of the present invention and shown in FIG. 1, the prosthetic device 40 shown in FIG. 2 can give a surgeon some further freedom to customize the size or the curvature of the device, in the event an "off-the-shelf" product does not satisfactorily fit the contour of the breast implant.

In this regard, reference should now be made to FIGS. 3*a*-3*d*, which illustrate how a surgeon might alter the prosthetic device 40 shown in FIG. 2 to fit and support a breast implant 125 having a smaller size than the prosthetic device was intended to fit. First, a surgeon can trim off a portion of the prosthetic device 40 by radially cutting along a width 39 of the front and back walls 42, 41 and the semi-circular periphery 43 of the semi-circular, toroidal shaped prosthesis 40, as illustrated by FIG. 3(*a*). After this one simple cut, the surgeon can slightly bend a remaining portion 35 of the prosthesis inwardly to then form a partial or semi-circular doughnut or toroidal-shaped portion 30 having a smaller radius, and affix the top edges of the smaller device to the chest wall and/or the capsule or surrounding tissue inside the surgical pocket of the removed breast implant using proper fixation means, such as suture stitches at several locations along the top edges 47, 44 of the front wall 42 and back wall 41, respectively, as denoted by an "X" shown in FIG. 3(*c*) of the drawings. The breast implant 125 is then at least partially inserted and fitted properly within the receiving space 9 of the slightly altered remaining semi-doughnut portion 30 without forming seams, folds or wrinkles.

The three-dimensional mesh prosthesis formed in accordance with the present invention can be used prophylatically to prevent, or post-operatively to repair, the displacement of breast implants used in reconstructive, massive weight loss or augmentation procedures. The semi-round embodiment shown in FIG. 1 or the semi-doughnut embodiment shown in FIG. 2 of the present invention can be used for preventing or repairing any of the three types of implant malpositions. In this regard, FIGS. 4, 5 and 6 illustrate how the semi-doughnut shaped prosthetic device 40 may be used for repairing the lateral, medial and "bottoming-out" displacements of breast implants 425, respectively.

Figure 4:
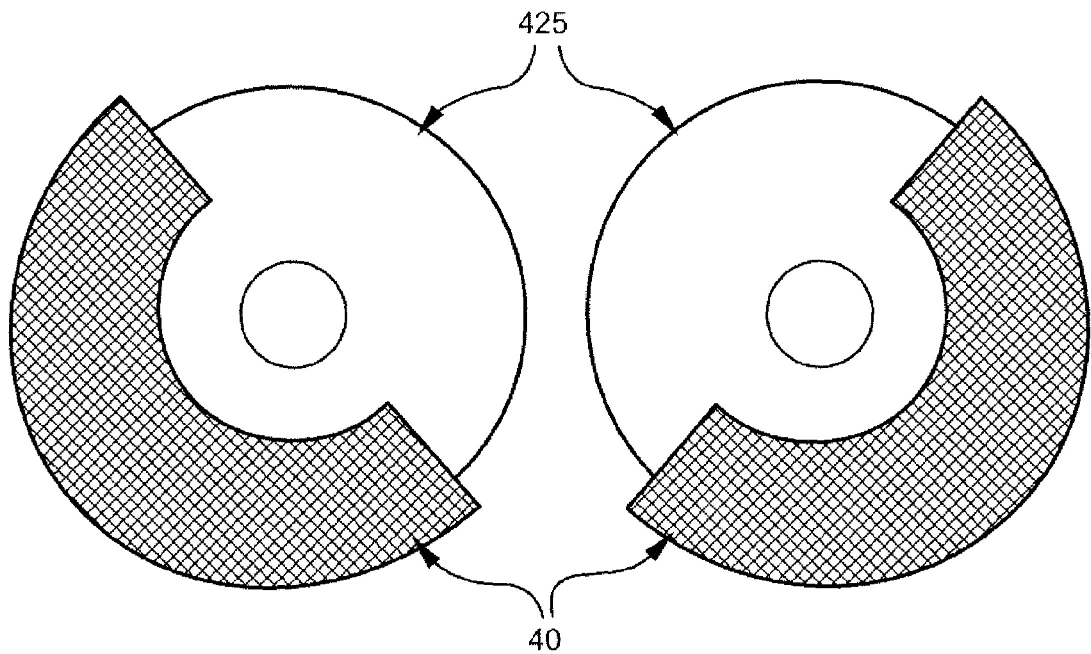
FIG. 4 is a front view of the semi-donut shaped, three-dimensional, seamless implantable prosthesis formed in accordance with the second embodiment of the present invention and illustrating the application of the prosthesis in correcting a breast implant displaced laterally.

More specifically, FIG. 4 illustrates the proper positioning of the preformed, three-dimensional prosthetic device 40 shown in FIG. 2 in repairing and maintaining the breast implants used in the left and right breasts which are laterally displaced, while preventing a "bottoming-out" displacement. Here, the prosthetic devices 40 are turned slightly outwardly of each breast in mirrored symmetry to one another so that they engage and at least partially receive in the space 9 the bottom and lateral outer sides (viewed from the patient's front) of the breast implants 425.

Figure 5:
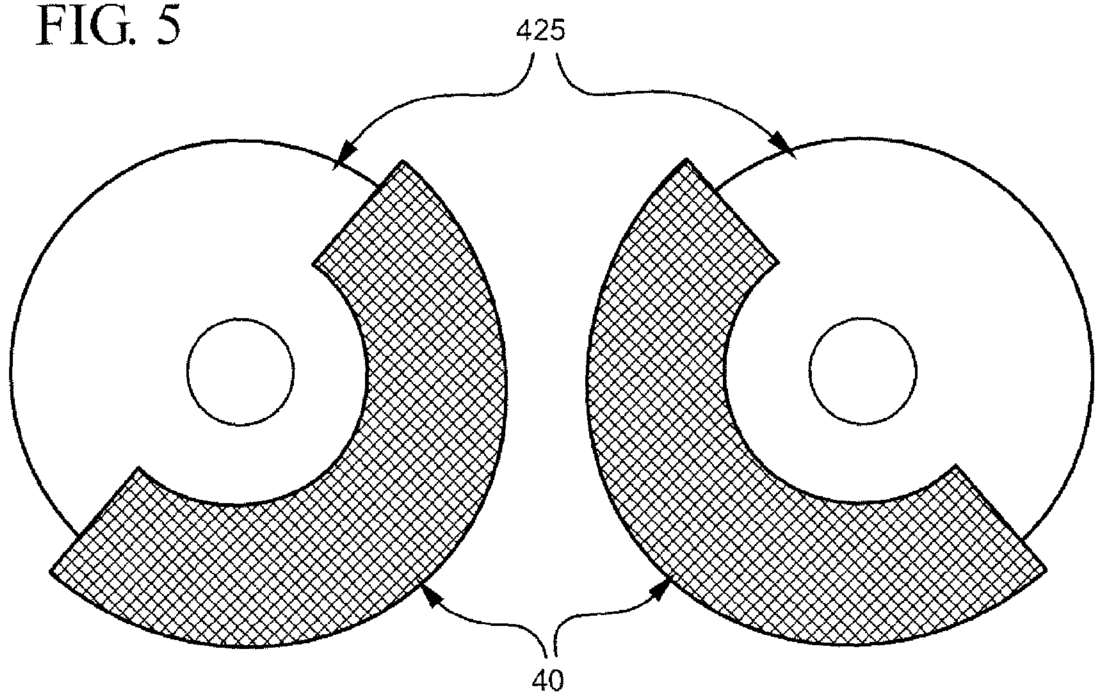
FIG. 5 is a front view of the semi-donut shaped, three-dimensional, seamless implantable prosthesis formed in accordance with the second embodiment of the present invention and illustrating the application of the prosthesis in correcting a breast implant displaced inferiorly.

FIG. 5 illustrates the preferred positioning of the prosthetic device 40 in repairing and supporting breast implants 425 which are displaced medially while preventing a "bottoming-out" displacement. Here, the prosthetic devices 40 are turned slightly inwardly on each breast in mirrored symmetry to one another so that each breast implant is at least partially received the receiving space 9 of a respective prosthetic device 40, which engages the bottom and inner sides (as viewed from the front of the patient) of the breast implants 425.

Figure 6:
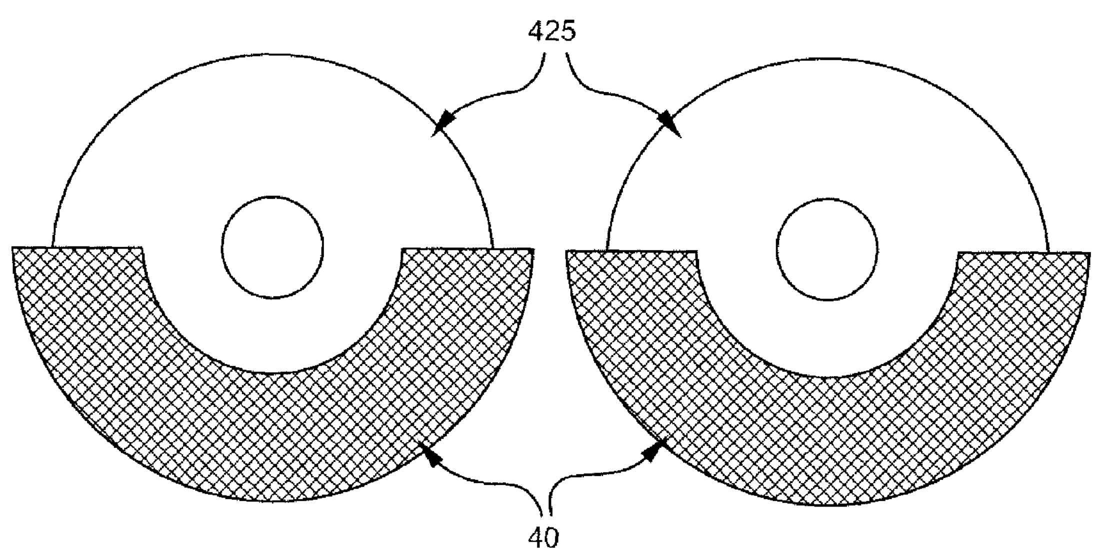
FIG. 6 is a front view of the semi-donut shaped, three-dimensional, seamless implantable prosthesis formed in accordance with the second embodiment of the present invention and illustrating the application of the prosthesis for repairing a breast implant experiencing "bottoming out" while restricting symmastia and lateral displacements.

Lastly, FIG. 6 illustrates the preferred positioning of the prosthetic device 40 of the present invention shown in FIG. 2 to repair a "bottoming-out" displacement, while restricting symmastia and lateral displacements of the breast implants. Here, it can be seen that the prosthetic devices 40 are situated on the patient to engage and support the bottom, left side and right side of the breast implants 425, which are at least partially received by the receiving space 9 formed between the front wall and the back wall 42, 41 of the prosthetic devices 40.

It should be realized, however, that in the case of repairing a displaced implant, if only one side is malpositioned, a surgeon may need only to repair the displaced side without disturbing the other side that is positioned normally.

The preformed, seamless, three-dimensional, anatomically contoured prosthetic device 10, 40 formed in accordance with the present invention is flexible enough to be folded or rolled up for ease of insertion through a relatively small incision into the surgical pocket formed for receiving the breast implant. It can be inserted in the surgical pocket of the breast implant through a periareolar or inframammary incision. It may also be possible to use a trocar to deliver the three-dimensional prosthetic device, after it is rolled up, in an endoscopic procedure performed using a transaxillary incision in the primary operation. However, if the prosthetic device 10, 40 is used for the post-operative repair of a dispositioned implant, it is preferable to use a periareolar or inframammary incision for the ease of deployment and fixation of the three-dimensional prosthetic device 10, 40.

As mentioned previously, the preformed, seamless, three-dimensional, anatomically contoured prosthetic device of the present invention is preferably formed from a mesh material 2 having a substantially uniform construction throughout. The mesh material 2, or other material from which the three-dimensional prosthetic device 10, 40 may be formed, may include a material which is bioabsorbable, partially bioabsorbable or completely nonabsorbable. For example, the prosthetic device 10, 40 of the invention may be formed from a bioabsorbable material, such as Polyglicolide (PGA), polylactide (PLA), copolymers of PGA/PLA, PGA/caprolactone, polydioxanone (PDS), or a completely nonabsorbable material such as Nylon, Polyethylene terephthalate (PET), polypropylene (PP), polyethylene (PE), their copolymers or blends, or a partially bioabsorbable material such as any combination of absorbable and non-absorbable materials.

Furthermore, the preformed, seamless, three-dimensional mesh prosthetic mesh device 10, 40 of the present invention can be fabricated by any known method, such as weaving or knitting, or other textile processes, to directly produce the desired three-dimensional shape. However, a preferred method of forming the prosthetic device 10, 40 of the present invention is a thermal forming process such as that described in the provisional patent application entitled "Preformed Support Device and Method and Apparatus for Manufacturing the Same" having as the named inventors thereof David Lindh and Etan Chatlynne, and filed concurrently herewith, the disclosure of which is incorporated herein by reference.

Figure 9:
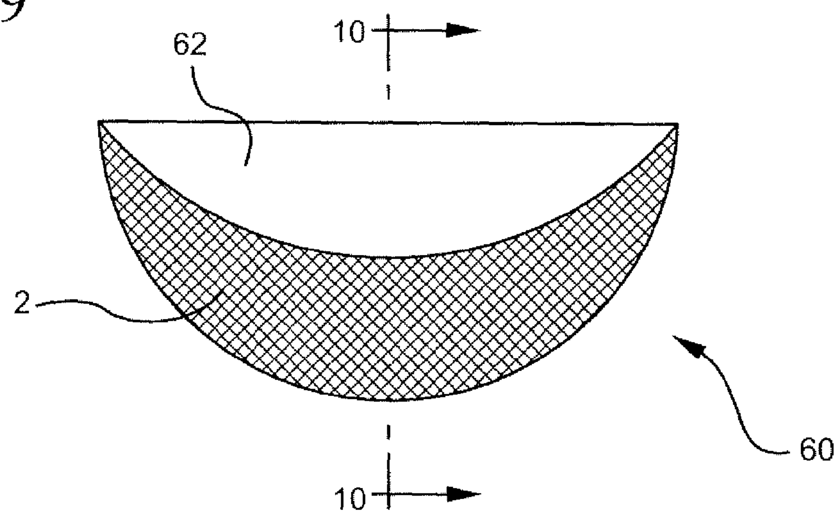
FIG. 9 is a front view of a semi-round, three-dimensional, seamless implantable prosthesis made of a laminated composite formed in accordance with the present invention.
Figure 10:
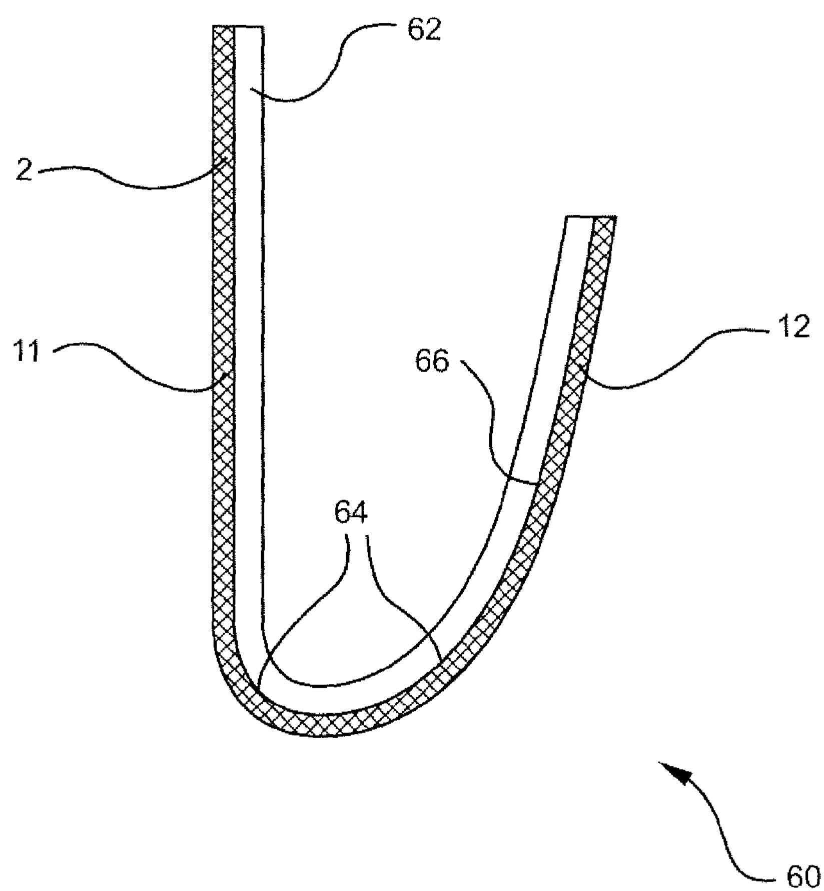
FIG. 10 is a cross-sectional view taken along the line 10-10 of FIG. 9 of the semi-round, three-dimensional, seamless implantable prosthesis shown in FIG. 9.

The three-dimensional prosthetic device 10, 40 of the present invention may also be made of a laminated composite, as shown in FIGS. 9 and 10. For purposes of illustration only, the prosthetic device 60, made of a laminated composite, has basically the same structure as the first or second embodiments of the prosthetic device 10, 40 shown in FIG. 1 or 2 of the drawings, respectively, and described previously, except for the laminated composite structure thereof. Therefore, components of the laminated prosthesis 60 which are the same as or similar to the components of the prosthetic device 10 described previously, which structure will be used herein to describe the features of prosthetic device 60 and the other embodiments of the prosthetic devices 80 and 100 to follow, will have like reference numbers.

For example, the three-dimensional prosthetic device 60 may be formed from a non-absorbable polypropylene mesh 2 that is laminated with a temporary shape-holding element 62. The temporary shape-holding element 62 may be an absorbable film or sheet material. The thickness of the absorbable shape-holding film 62 is preferably in the range of about 0.004 inches to about 0.040 inches so that the laminated device 60 is flexible enough to be folded or rolled up during deployment of the prosthetic device 60 and yet is rigid enough to unfold by itself after being delivered to the surgical pocket of the breast implant and maintain the preformed, three-dimensional, anatomically contoured shape during the surgical procedure and thereafter until absorbed by the patient's body. The temporary shape-holding element 62 may preferably further be made from a bio-absorbable thermal plastic polymer having a low softening or melting temperature. A low softening or melting temperature allows the temporary shape-holding element 62 to be laminated to the mesh material 2 at a relatively low temperature with minimal or no effect on the properties of the mesh material 2. The temporary shape-holding element 62 may maintain a certain strength for about three weeks to about six weeks, for example, while the patient's tissue is growing into and integrating with the porous mesh 2 of the prosthetic device 60. It is preferable for the temporary shape-holding material 62 to be essentially absorbed by the patient's body within a period of about six months or less from the time it is implanted in the patient. In this manner, the only material remaining after the temporary shape-holding material 62 is absorbed is the relatively soft, non-absorbable mesh material portion 2 of the prosthetic device 60, which will have minimal or no palpability while providing long lasting support to the tissue and breast implant.

Figure 8:
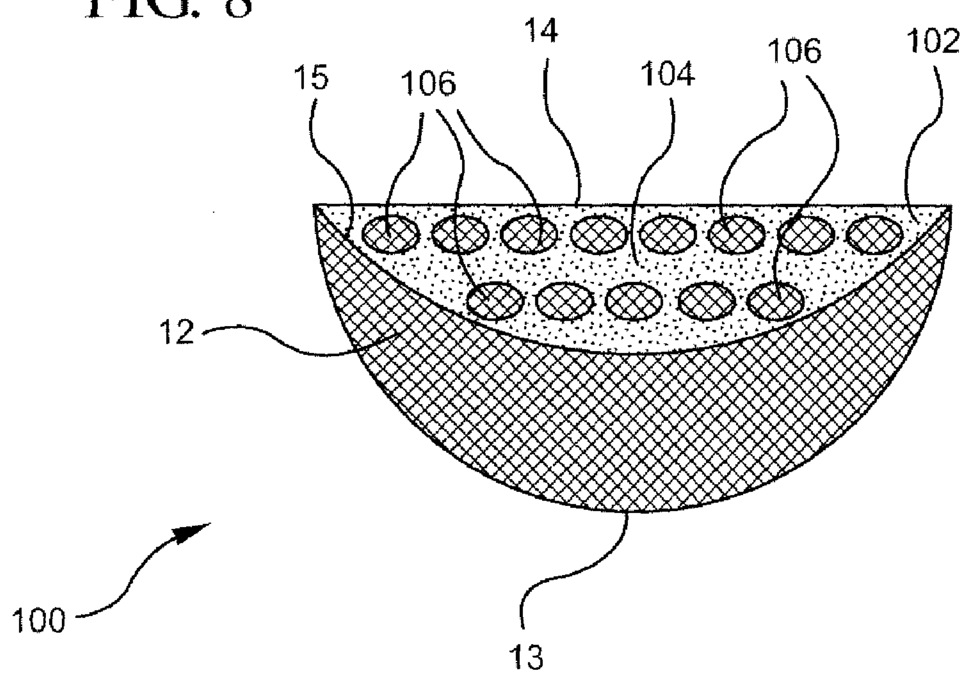
FIG. 8 is a front view of the semi-round, three-dimensional, seamless implantable prosthesis formed in accordance with the first embodiment of the present invention and having a distinguishing colored and perforated portion situated thereon.

As can be seen from FIGS. 9 and 10 of the drawings, the temporary shape-holding element 62 is preferably laminated to the mesh material 2 of the prosthetic device 60 from the inside of the prosthesis 60, that is, preferably within the receiving space 9 defined between the front wall 12 and the back wall 11, so that the temporary shape-holding element 62 may be directly facing or in contact with the breast implant. The temporary shape-holding element 62, and in particular the bio-absorbable sheet material from which the element is formed, has a thickness that is preferably in the range of about 0.008 inches to about 0.015 inches. The shape-holding element 62 may be laminated to the mesh material 2 of the prosthetic device 60 to cover the entire mesh material 2 or only a portion of the three-dimensional mesh device. One possible variation of such structure is to have only the back wall 11 and transitional corners 64 laminated with a bio-absorbable film while keeping the main portion 66 of the front wall 12 unlaminated, as shown in FIGS. 9 and 10 of the drawings. It may be further preferable that the mesh element 2 be laminated from both sides with temporary shape-holding elements 62 to provide increased rigidity and allowing the laminates to bond to each other through openings in the mesh thereby sandwiching the mesh securely in place. It is also preferred to have some openings in the temporary shape-holding element 62, as shown in FIG. 8, as the mesh material from which the prosthetic device 60 is preferably formed has a multiplicity of openings formed through the thickness thereof.

Figure 11:
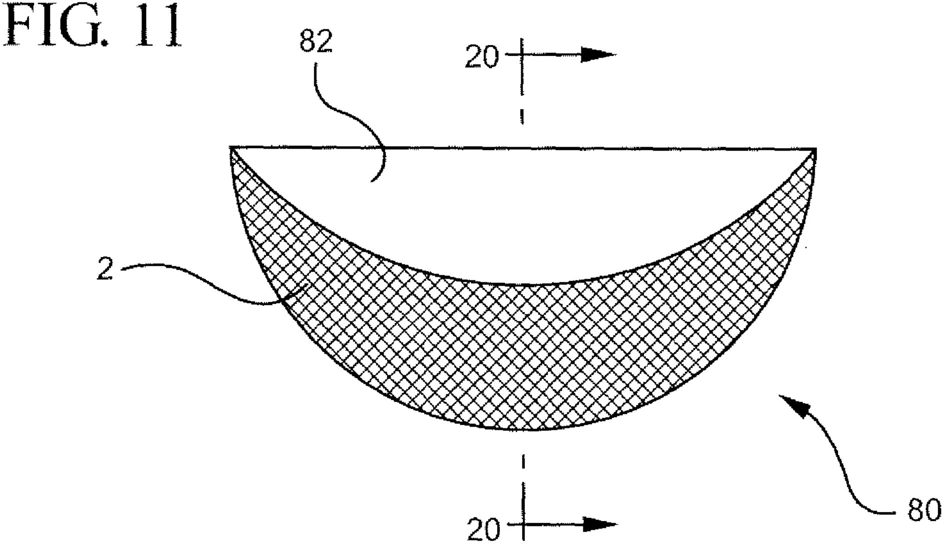
FIG. 11 is a front view of a semi-round, three-dimensional, seamless implantable prosthesis having a temporary shape-holding element and means for removal thereof formed in accordance with the present invention.
Figure 12:
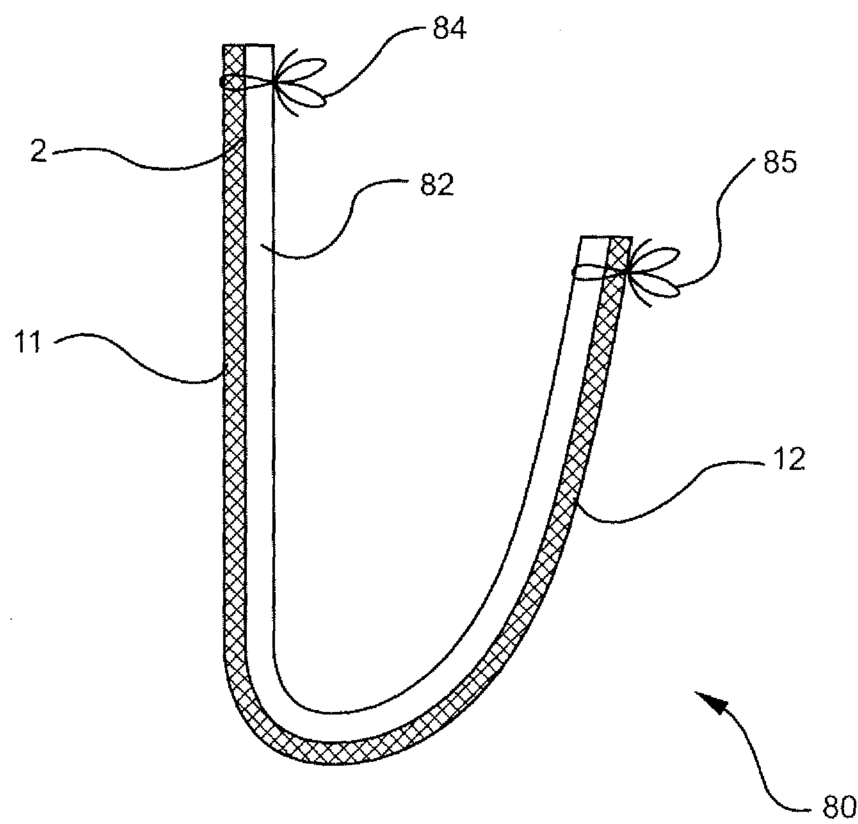
FIG. 12 is a cross-sectional view taken along the line 20-20 of FIG. 11 of the semi-round, three-dimensional, seamless implantable prosthesis shown in FIG. 11.

The temporary shape-holding element 62 may also be formed from a non-absorbable material, such as polypropylene film or sheet material. The shape-holding material 62 can be temporarily attached to the three-dimensional mesh portion 2 of the prosthetic device 60 to keep the three-dimensional device from being deformed or collapsed during storage or during the surgical procedure to implant the prosthetic device 60, but removed prior to completion of the implantation procedure. Accordingly, and as shown in FIGS. 11 and 12 of the drawings, a three-dimensional prosthetic device 80 formed in accordance with the present invention includes a mesh material 2 that defines all of the components of the first and second embodiments of the prosthesis 10, 40 shown in FIGS. 1 and 2, and a shape holding material 82 that is temporarily affixed to the mesh material 2 of the prosthetic device 80 and removable therefrom. For this purpose, an attaching means, such as sewing threads 84 and 85, may be joined to the temporary shape-holding element 82, and by loosening or releasing the sewing threads 84 and 85, the temporary shape-holding element 82 may be removed from the mesh material 2 forming the three-dimensional prosthetic device 80 after the prosthetic device 80 is properly positioned and affixed to the patient's tissue.

Figure 13:
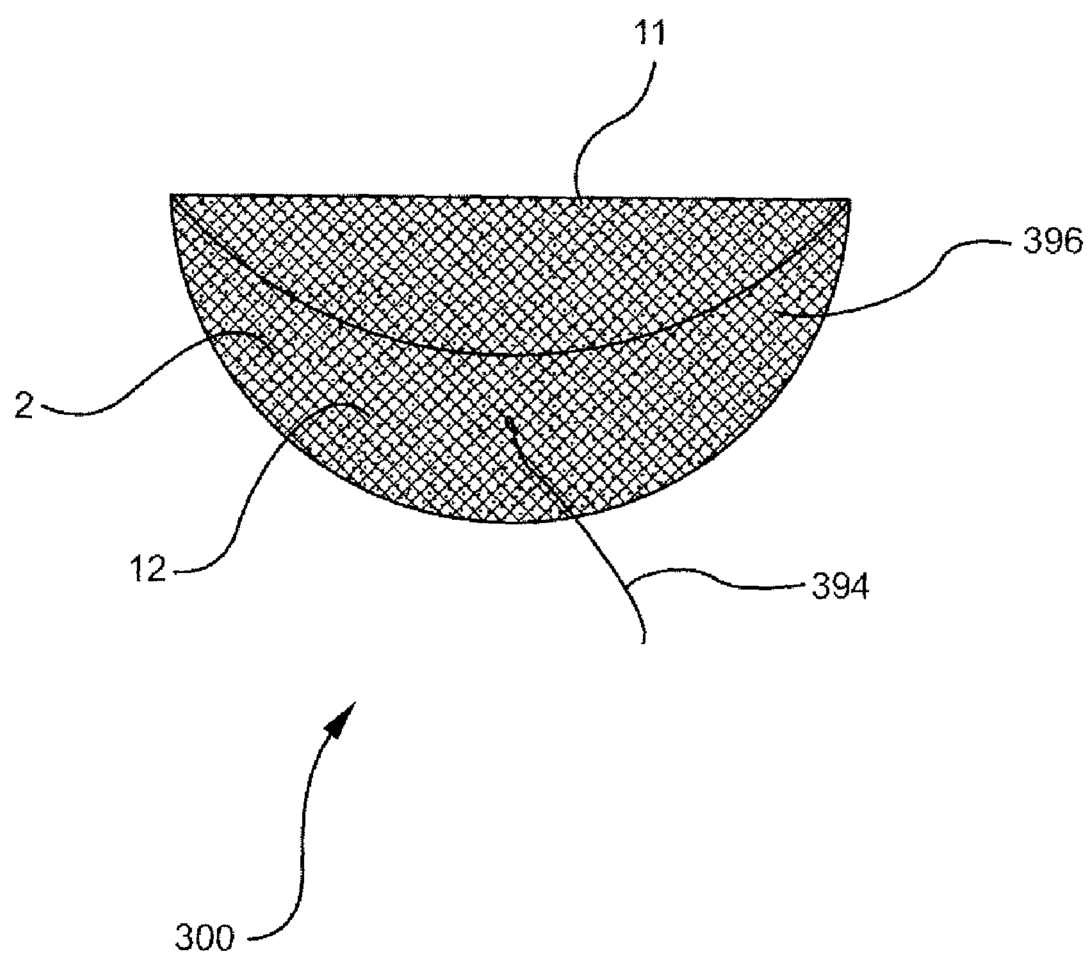
FIG. 13 is a front view of a semi-round, three-dimensional, seamless implantable prosthesis having a coating agent and/or a temporary pulling string thereof formed in accordance with the present invention.

Alternatively, and as shown in FIG. 13 of the drawings, the mesh material 2 from which the seamless, three-dimensional, anatomically contoured prosthetic device 300 is formed may be coated with a film or agent 396 that keeps the mesh material 2 from sticking together when wetted by body fluids. Or, the mesh material 2 of the three-dimensional prosthetic device 300 may be coated with a film or agent 396 that helps prevent body fluids from adhering to the mesh material 2 to avoid the mesh material from becoming weighed down by the extra weight of the body fluids that may collect on it and within the pores and interstices of the mesh material 2 of the prosthetic device 300. When the mesh material 2 becomes wet and sticks together, the attaching means (e.g., sewing thread or string 394) described earlier may be attached to the front wall 12 or to another component or wall of the prosthetic device 300, and may be pulled to separate the front wall 12 from the back wall 11 and keep the walls 11, 12 separated until the prosthetic device 300 is properly deployed and implanted in the patient's body.

Figure 14A:
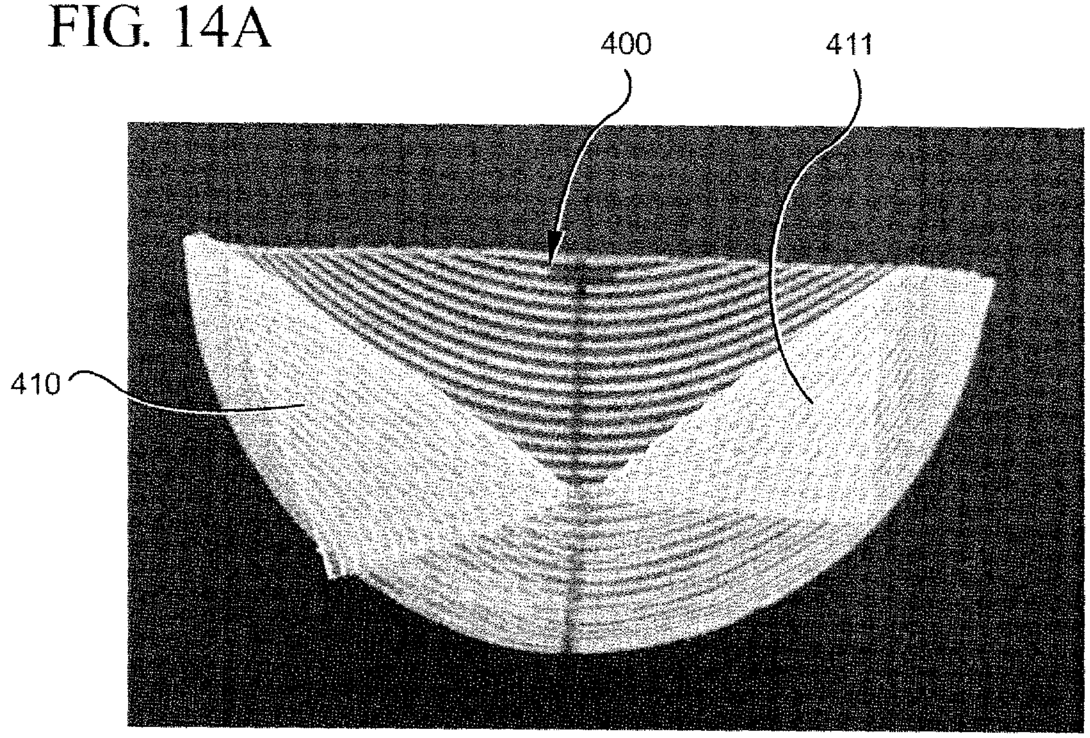
FIG. 14 is a front view of a semi-round, three-dimensional, seamless implantable prosthesis having temporary folded flaps on front wall in accordance with the present invention.
Figure 14B:
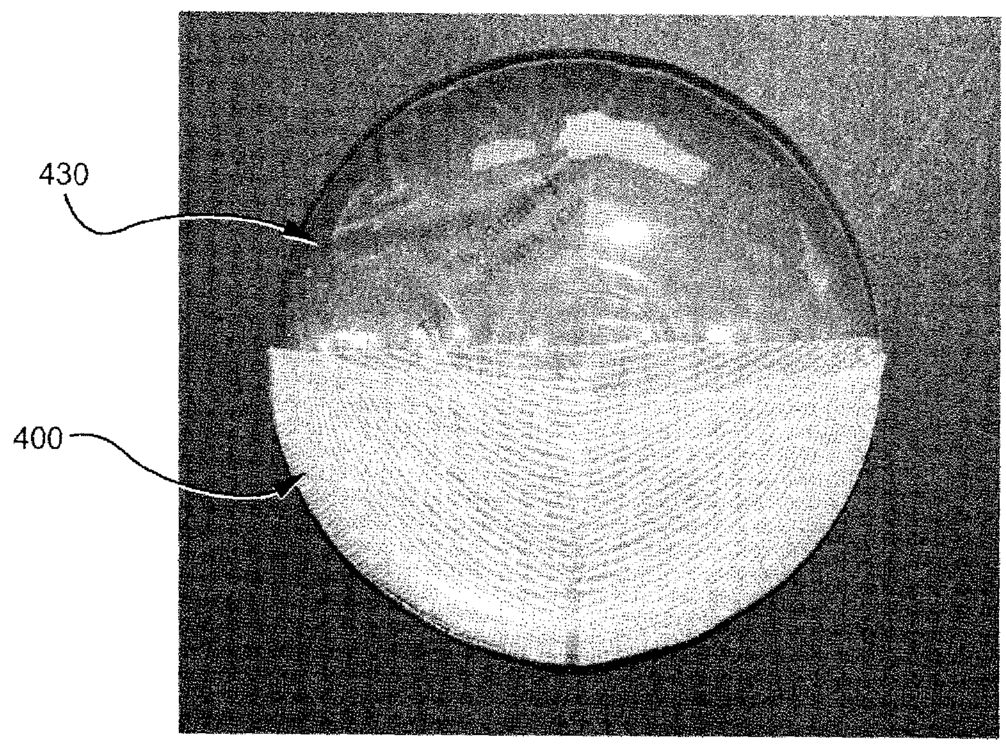

Referring to FIG. 13, a sewing thread, such as a suture 394, may also be configured as a temporary way to maintain the shape of the prosthetic device 10 during implantation. In a similar manner, a sewing thread may also be used to temporarily adjust the dimensions of sections of the prosthetic device 300. This may be achieved by fixing one end of the suture to the mesh material 2 at one location and then fixing the other end of the suture at a second location such that the distance between the suture ends is less than that of the surface length of the section of mesh 2 that extends between the two fixed suture ends. In this configuration, the suture will cause the surface of the underlying mesh to buckle and, by doing so, will result in the mesh position to be biased in one direction. If one of the suture fixation points utilizes a one-way suturing retaining device, as is disclosed in U.S. Pat. Nos. 5,669,935 and 7,083,637, which are incorporated in their entirety by reference herein, the suture may be further tensioned to increase the biasing of the mesh. When no longer needed, the suture may be removed to release tension in the mesh 2. The suture may be released by, for example, cutting or untying the suture ends. If absorbable, the cut ends may be left behind. The suture may also be positioned and cut so that one cut end may be later tied to a free end of a similar tensioning suture that is cut at another location on the mesh 2 to allow for the respective free ends of the suture to be tied to each other. This can be advantageous when the mesh design 2 is such that it provides for flaps 410, 411, that are temporarily folded to allow for easy access to the back wall 11 so that the back wall 11 may be attached to the tissue as shown in FIG. 14(*a*). FIG. 14(*b*) shows a breast implant placed inside the device 400 when flaps 410 and 411 are brought together. The effective front wall becomes as high as or higher than the back wall after the device is properly implanted.

Figure 7:
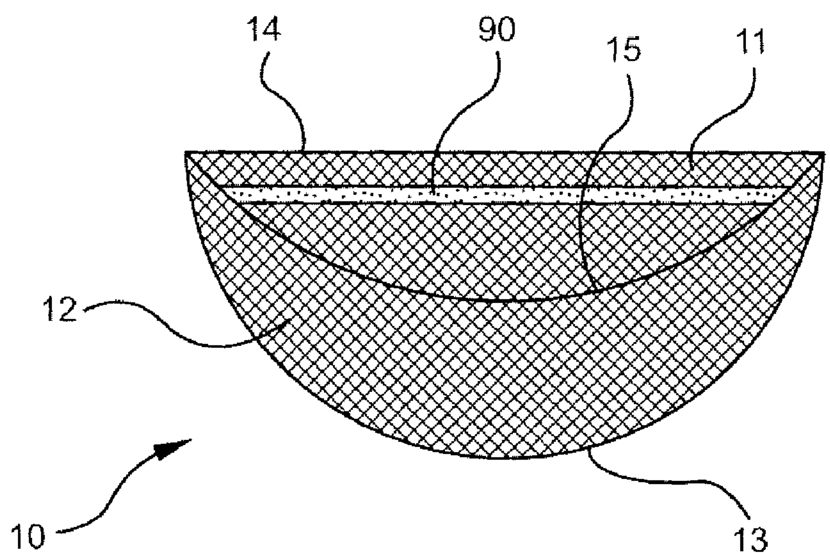
FIG. 7 is a front view of the semi-round, three-dimensional, seamless implantable prosthesis formed in accordance with the first embodiment of the present invention and having a colored strip added thereto.

The three-dimensional prosthetic device of the present invention may have its natural color or may be formed with other colors. For example, in order to distinguish the back wall 11 from the front wall 12, the back wall 11 (or front wall 12) may include one or more colored stripes 90 on the entire prosthetic device or over a portion of the prosthetic device. As illustrated by FIG. 7 of the drawings, a colored stripe 90 is added to the back wall 11 of the three-dimensional prosthetic device. The stripe 90 may be formed directly on the mesh material 2 from which the prosthetic device is preferably formed. Alternatively, a separate mesh strip, having a different color from that of the mesh material 2 of the prosthetic device, may be attached to the mesh material 2 to help differentiate the back wall 11 from the front wall 12 to facilitate the physician's use and deployment of the prosthetic device. Alternatively, a different indicator for distinguishing the back wall 11 from the front wall 12 may be used on the prosthetic device, such as a colored biocompatible thread (not shown) which can be simply sewn to the mesh material 2 of the three-dimensional prosthetic device before or after it is formed.

Figure 15A:
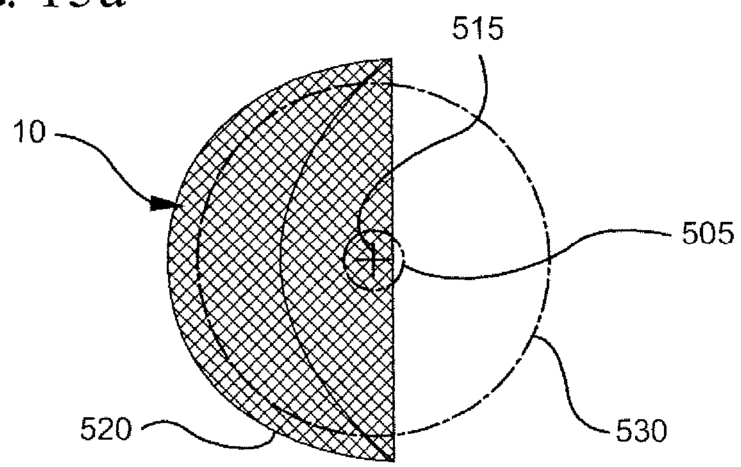
FIG. 15 shows anterior views of a semi-round, three-dimensional, seamless implantable prosthesis having center mark "+" oriented at different positions while the center of the device is aligned with the center of the breast implant.
Figure 15B:
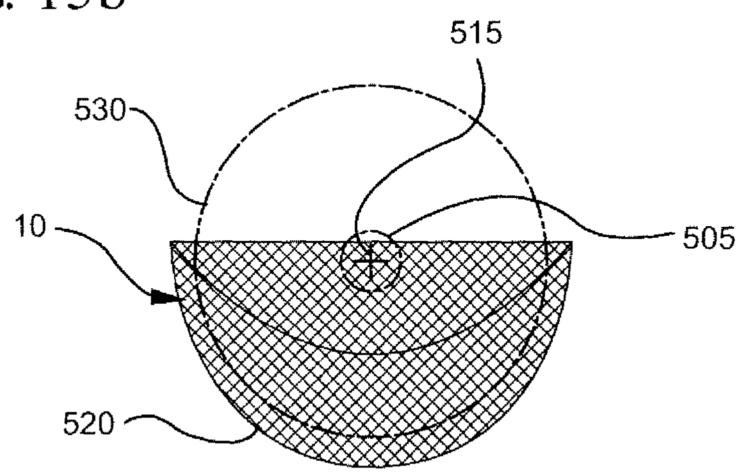
Figure 15C:
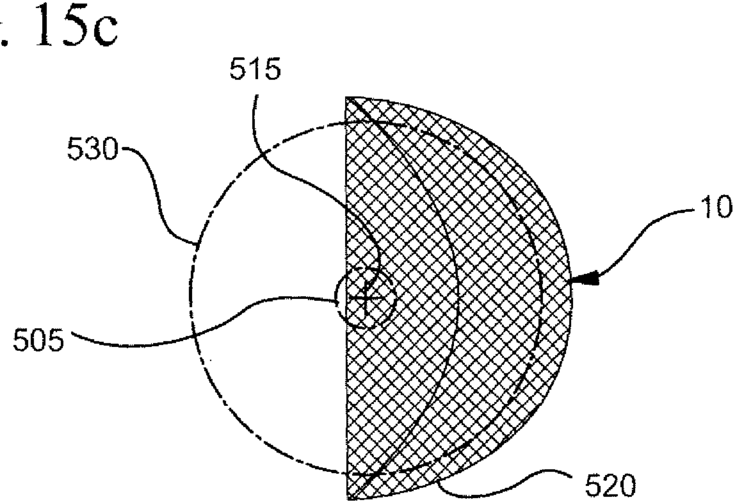

Referring to FIG. 15, it is further preferred that the geometric center is identified with a mark such as a "+" sign 515 on the back wall 11 of device 10. When the center mark 515 of the device 10 is aligned approximately with the nipple position or where the center ring 505 of the breast implant is expected to be, the peripheral of the device 10 will be automatically defined, for a given radius of the device selected. FIG. 15 shows that, when the center mark 515 of the device is aligned and fixated approximately with the expected center 505 of the breast implant, the peripheral edges 520 of the device 10 will naturally conform the contour 530 of the breast implant no matter how the device is oriented because the radius or curvature of peripheral of the device 10 is constant. In this way, when positioning and locating the device, a surgeon has no need to fixate the peripheral edges 520 of the device 10, which may be required otherwise before fixating the back wall of the device.

If the three-dimensional prosthetic device is partially laminated, such as described previously and shown in FIGS. 9 and 10 of the drawings, it is preferable to have the back wall 11 laminated with a different color from that of the mesh material 2 used for the front wall 12 so that it will be easier for the surgeon to distinguish the front wall 12 from the back wall 11 during deployment of the prosthetic device. FIG. 8 is a front view of a semi-round, three-dimensional composite mesh prosthetic device 100 having a similar structure to that of the prosthetic device 10 of the first embodiment shown in FIG. 1 of the drawings, except that the back wall 102 is formed to have a distinguishing color and is preferably perforated with a plurality of openings 106. The colored, more rigid back wall

102 can be formed by laminating a colored, perforated sheet 104 of a bioabsorbable polymer material to the mesh material 2 forming the prosthetic device 100, the mesh material 2 having a natural color or a color different from that of the perforated sheet 104 of bioabsorbable polymer added to the back wall 102.

Although variations of the first embodiment of the prosthetic device 10 shown in FIG. 1 of the drawings is used in facilitating the description of the alternate embodiments of the prosthetic devices 60, 80 and 100 shown in FIGS. 7-11, and that like reference numbers used in FIGS. 7-11 refer to the same or similar components of the prosthetic device 10 shown in FIG. 1, it should be realized that the variations and modifications of the prosthetic devices 60, 80 and 100 shown in FIGS. 7-11 are applicable to the prosthetic device 40 shown in FIGS. 2-5, i.e., the semi-circular, toriodally-shaped prosthetic device.

The prosthesis of the present invention described herein may be available in various sizes. This can reduce the duration of a particular surgical procedure, as there is little or no need to alter or manipulate the size or shape of the prosthetic device when it is properly selected for a given implant. The smoothly curved bottom periphery 13 of the three-dimensional mesh prosthetic device provides a natural fit to the contour of the breast implant supported thereby without requiring cutting or trimming in the operating room.

Furthermore, the three-dimensional prosthetic device of the present invention, and in particular the semi-doughnut (semi-circular toroidally-shaped) prosthesis 40 shown in FIGS. 2-5 of the drawings, easily accommodates implants of various sizes, shapes or projections, requiring minimal or no alteration of the prosthetic device during the surgical procedure. The absence of seams, folds or wrinkles in the preformed, three-dimensional prosthetic device of the present invention minimizes or eliminates palpability, bacterial hosting and the risk of infection. A flat back wall, which is preferred to be used on the prosthetic device, promotes ease of handling, storage or deployment during the implantation procedure.

Furthermore, the preformed mesh of the three-dimensional prosthetic device of the present invention has a resiliency which is sufficient to support its own weight and to maintain its shape in storage and during the surgical procedure. Furthermore, in a preferred form of the present invention, the three-dimensional prosthetic device includes a temporary shape-holding element attached to the mesh material from which the prosthetic device is formed to further increase the rigidity of the three-dimensional mesh prosthetic device.

In another embodiment of the present invention, the shape-holding material may be removed upon completion of the fixation of the prosthetic device in the patient, and the device may further include a coating agent or a pulling string which will help the device from sticking together during its deployment.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A preformed, seamless, three-dimensional, anatomically contoured prosthetic device for reinforcing breast tissue and supporting a breast implant, consisting of:

a back wall, the back wall having an upper rim and a bottom portion situated opposite the upper rim; and a front wall, the front wall having an upper edge and a bottom portion situated opposite the upper edge, the bottom portion of the front wall being joined to the bottom portion of the back wall to define a smoothly curved, seamless bottom periphery to the prosthetic device, the front wall being spaced apart from the back wall to define therebetween a receiving space for at least partially receiving and supporting a breast implant therein, wherein the back wall is substantially flat and the front wall is concave, wherein the prosthetic device is adapted to be implanted within a breast pocket of a patient such that the back wall is positioned adjacent to the chest wall or muscles overlaying the chest wall, wherein said prosthetic device has resiliency sufficient to independently support its own weight and to maintain its shape prior to implantation, wherein the prosthetic device is formed of a biocompatible mesh having a substantially uniform construction throughout, and wherein the prosthetic device is shaped using a thermal forming process.

2. A prosthetic device as defined by claim 1, wherein the upper edge of the front wall is curved, and wherein the height of the front wall is less than the height of the back wall.

3. A prosthetic device as defined by claim 1, wherein the back wall and the front wall are joined together to provide the prosthesis with a semi-circular, toroidal shape.

4. A prosthetic device as defined by claim 1, wherein the front wall and the back wall are formed from a mesh material, wherein the mesh material is a thermal formable polymer.

* * * * *